United States Patent [19]

Broddner et al.

[11] Patent Number: 4,657,008
[45] Date of Patent: Apr. 14, 1987

[54] ANESTHESIA AND/OR RESPIRATOR APPARATUS HAVING A MOISTENING AND/OR GASIFICATION CHAMBER

[75] Inventors: Sven M. Broddner, Upplands Vasby; Leif B. Hogman, Vallingby; Rune Nyman, Solna; Lars Klintholm, Spanga, all of Sweden

[73] Assignee: Gambro Engstrom AB, Sweden

[21] Appl. No.: 748,542

[22] Filed: Jun. 25, 1985

[30] Foreign Application Priority Data

Jun. 28, 1984 [SE] Sweden .................. 8403447

[51] Int. Cl.⁴ .................................. A61M 16/00
[52] U.S. Cl. ..................... 128/203.27; 128/200.19; 128/203.14
[58] Field of Search ............... 128/200.19, 201.21, 128/203.14, 203.17, 203.25, 203.27

[56] References Cited

U.S. PATENT DOCUMENTS

| | | | |
|---|---|---|---|
| 3,863,630 | 2/1975 | Cavallo | 128/203.27 |
| 4,051,205 | 9/1977 | Grant | 128/203.27 X |
| 4,201,204 | 5/1980 | Rinne et al. | 128/203.27 |
| 4,215,409 | 7/1980 | Strowe | 128/203.14 X |
| 4,484,576 | 11/1984 | Albarda | 128/202.22 |

FOREIGN PATENT DOCUMENTS

| | | |
|---|---|---|
| 0106015 | 4/1984 | European Pat. Off. . |
| 2240659 | 8/1972 | Fed. Rep. of Germany . |
| 3116951 | 4/1981 | Fed. Rep. of Germany . |
| 3234474 | 9/1982 | Fed. Rep. of Germany . |
| 1085472 | 8/1972 | Sweden . |

Primary Examiner—Stephen F. Husar
Attorney, Agent, or Firm—Lerner, David, Littenberg, Krumholz & Mentlik

[57] ABSTRACT

Anesthesia and/or respirator apparatus is disclosed which includes a moistening and/or gasification chamber. The chamber is constructed such that liquid intended to be gasified or evaporated can be received from a source through a metering valve. In the preferred embodiment, the gasification chamber includes a heatable plate or the like for the heating of the supplied liquid. The apparatus means further includes a microprocessor for measuring the energy which is used for the gasification as a measure of the quantity of liquid supplied. In this regard, if certain defined functions are not fulfilled, an alarm signal is generated.

25 Claims, 2 Drawing Figures

ANESTHESIA AND/OR RESPIRATOR APPARATUS HAVING A MOISTENING AND/OR GASIFICATION CHAMBER

FIELD OF THE INVENTION

The present invention relates in general to an anesthesia and/or respirator apparatus suitable for supplying a gas stream mixture containing a gasified liquid to a patient through a ventilator section. More particularly, the present invention relates to such an apparatus including a moistening and/or gasification chamber which is adapted so that one or more liquids intended to be gasified or evaporated can be supplied to the chamber from a respective sources containing such liquids. Still more particularly, the apparatus supplies the liquids through one or more metering valves under the control of a microprocessor which is responsive to changed conditions in the gasification chamber.

Yet more particularly, the present invention is intended primarily to be used on a complete anesthesia arrangement. It will, however, be clear to those skilled in this art that in many respects this apparatus can also be applied more generally, for example, for the moistening of respiratory gases in a respirator.

BACKGROUND OF THE INVENTION

Known anesthesia and/or respirator systems frequently suffer from a disadvantage, in that they are technically complicated and therefore become quite expensive. Of course, simpler and/or cheaper systems do exist, but in many cases these systems are then considered to be unreliable or just cannot fulfill the functions to which they are normally required to perform. Furthermore, there is presently unavailable an apparatus which includes simple means for the reliable measurement of the quantity of liquid being supplied for gasification or evaporation, and which controls the supply of such liquid to a gasification chamber through one or more metering valves.

SUMMARY OF THE INVENTION

In accordance with the preferred embodiment of the present invention, there is disclosed an apparatus for supplying a gas stream to a patient. The apparatus includes a source of a propellant gas; storage means for storing a gasifiable liquid; pressure means in fluid communication with the source for maintaining the liquid within the storage means under a pressure provided by the propellant gas, the liquid being supplied from the storage means in response to the pressure; a gasification chamber including a liquid inlet for receiving the liquid from the storage means, a gas inlet for receiving the propellant gas from the source and a gas stream outlet, the gasification chamber gasifying the liquid in the presence of the propellant gas to provide a gas stream therefrom to be supplied through the gas stream outlet to a patient; and metering means arranged between the fluid inlet and the storage means for metering the quantity of the liquid being supplied by the pressure means from the storage means to the gasification chamber.

In accordance with the disclosed embodiment, the propellant gas maintaining the liquid under a pressure and the propellant gas provided to the gasification chamber are supplied from a common source, and wherein the gasification chamber includes a heatable plate for heating the liquid to be gasified. Further, temperature means are provided for measuring the temperature of the heatable plate and wherein the storage means comprises a flask having an opening for receiving the pressure means therein. Still further, the metering means is operable during a plurality of periods, whereby the supplying of the liquid from the storage means to the gasification chamber is a function of the duration of these periods.

Further in accordance with the disclosed embodiment, there is provided a plurality of storage means for each storing a gasifiable liquid to be supplied to the gasification chamber, and wherein the plurality of storage means are connected alternatively to the liquid inlet of the gasification chamber. Further, the plurality of storage means are connected to the liquid inlet through a common metering means or separately connected to the liquid inlet through a corresponding number of metering means.

Further in accordance with the disclosed embodiment, there is provided means for measuring the energy used for gasifying the liquid by the gasification chamber for determining the quantity of liquid being supplied thereto from the storage means, and control means for generating an alarm signal when the amount of energy measured differs from a predetermined limit value. Still further, there is provided adjustment means for adjusting the predetermined limit value in relationship to the flow of the gas stream through the gasification chamber, and wherein the limit value comprises a low limit value and a high limit value.

Further in accordance with the disclosed embodiment, there is provided temperature means for measuring the temperature of the gasification chamber, and control means for generating an alarm signal when the value of the temperature measured differs from a predetermined limit value.

By utilization of the present invention, an anesthesia and/or respirator apparatus is obtained, which is constructed to include means for measuring the energy which is used for the gasification process as a measure of the quantity of liquid being supplied. As will be evident from a description of the anesthesia and/or respirator apparatus of the present invention, this energy measuring can be achieved in a very simple, but nevertheless, reliable manner.

Specifically, the gasification chamber of the present invention includes a heatable plate or the like for heating of the liquid being supplied for gasification. The energy supplied to the plate, at a constant temperature of the plate, corresponds directly to the measure of the quantity of the liquid being supplied. This measured quantity of liquid can be be corrected by taking into consideration the quantity of gas flowing through the chamber and the temperature within the chamber itself. Preferably, the source of liquid to be gasified is arranged in a storage device which is maintained under pressure. At the same time, the stored liquid is provided in fluid communication with the gasification chamber via a mechanically and/or manually openable metering valve. By adapting the metering valve so that it can be opened during a number of short periods, the metering operation is simply a function of the opening frequency or cycle duration.

In accordance with a preferred embodiment of the present invention, which has multi-purpose application, the liquid source comprises one of a number of such storage devices which are connected alternatively to the gasification chamber via a common metering valve or to a number of separate metering valves. A simple and inexpensive design is achieved by constructing the liquid source as a flask connected to the gasification chamber via one or more metering valves. In order to make possible an adjustment of the temperatures present in the gasification chamber, means are provided for measuring either the temperature of the gasification chamber or that of the heatable plate. In this regard, means are provided for generating an alarm signal when the amount of energy measured and/or the temperature measured exceeds or remains below certain predetermined limit values. At the same time, means are provided for adjusting the alarm limits in relationship to the gas flow through the gasification chamber.

Further, in order to avoid any disturbance of the measurements by non-gasified liquid present within the gasification chamber, means are provided for the collection of such liquid, e.g., stabilizing agent, which is not intended to be gasified.

Still further, if the liquid source is obtained from a plurality of storage devices, each of these storage devices can be provided with a level indicator which is adapted to indicate the level of the liquid source on a display common to these indicators.

In practice, it has been found preferable to provide that an alarm signal be generated when $$\left| P_B\ddot{O}_R - P_{EL} \right| > K_4 + K_5 \times P_B\ddot{O}_R,$$

with $P_B\ddot{O}_R = P_O + K_1 \times F + K_2 \times M + K_3 (F,M)$ where:

$P_0$, $K_1$ and $K_2$ are measured constants,

F is the total gas flow through the gasification chamber,

M is the quantity of liquid injected per unit of time, $K_3$ is a measured correction value which is measured and stored in tabular form and which is a function of F and M in combination, $K_4$ and $K_5$ are constants which are determined by trial measurements, $P_{B\ddot{O}R}$ is the effect which is needed to keep the heating element at a constant temperature by the supply of the desired amount of liquid intended to be gasified or evaporated, and where $P_{EL}$ is the corresponding measured value for the aforementioned effect.

Further, safety is achieved if the apparatus of the present invention is designed such that an alarm signal is generated when $$\left| U_T - K_6 \right| > K_7 + K_8 \times P_B\ddot{O}_R,$$

when $K_6$, $K_7$ and $K_8$ are constants which are determined by trial measurements, and $U_T$ is the voltage measured of a thermistor adapted to measure the temperature of the heatable plate.

BRIEF DESCRIPTION OF THE DRAWINGS

The enclosed drawings illustrate a preferred embodiment of the anesthesia and/or respirator apparatus in accordance with the present invention, and in these drawings.

DETAILED DESCRIPTION

Figure 1:
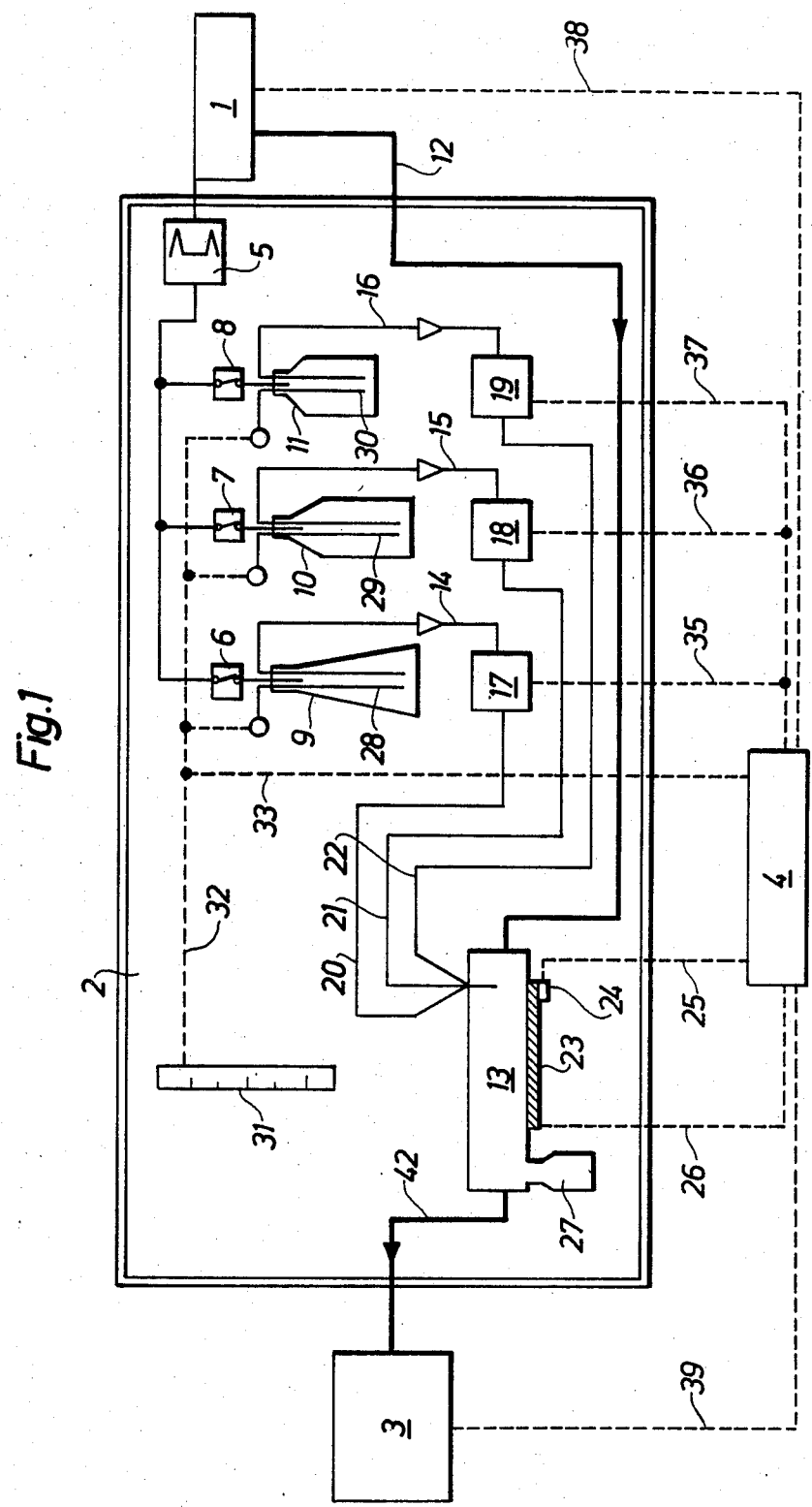
FIG. 1 is a diagrammatic, block diagram of a portion of a complete anesthesia arrangement in accordance with the present invention.
Figure 2:
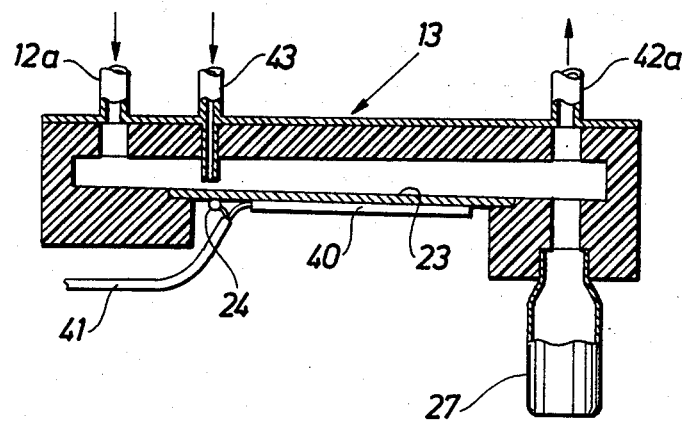
FIG. 2 is a cross-sectional view of the gasification chamber included in the complete anesthesia arrangement.

The present invention can be more fully understood with reference to FIGS. 1 and 2 which demonstrate a preferred embodiment thereof. The anesthesia arrangement, as shown in FIG. 1, is constructed of three parts, namely, a gas plate 1 for generating a propellant gas, a gasification arrangement generally designated by reference numeral 2, and a ventilation section 3 by means of which the prepared gas is conducted to a patient which is not shown on the drawing. All three of these parts are controlled, as indicated by broken lines, by a microprocessor 4 or the like. The gas plate 1, ventilator section 3 and microprocessor 4 have been shown in FIG. 1 in the form of designated blocks, whereas the gasification arrangement 2 has been shown in somewhat greater detail.

The propellant gas from the gas plate 1 is supplied by a reducing valve 5 and one or more valves 6, 7 and 8 to one or more flasks 9, 10 and 11 which contain a liquid anesthetic. Furthermore, the propellant gas from the gas plate 1 is also supplied by a duct 12 directly to a gasification chamber 13.

The flasks 9, 10 and 11 are maintained under a pressure provided by the propellant gas, so that the liquid contained in the flasks can be supplied by the ducts 14, 15 or 16 and any one of the valves 17, 18 or 19 and corresponding ducts 20, 21 and 22 to the gasification chamber 13. The gasification chamber 13 is constructed to include a heatable plate 23 for the gasification of the liquid anesthetic supplied from the flasks. The temperature of the plate 23 is sensed by a thermistor 24. The sensed temperature is transmitted to the microprocessor 4, as indicated by the broken line 25. In the same manner, the microprocessor 4 is adapted to control the heating of the plate 23, as indicated by the broken line 26. Further, the gasification chamber 13 contains a collecting device 27 for liquid not intended to be gasified, e.g., a stabilizing agent such as thymol.

The flasks 9, 10 and 11 are each provided with a level indicator 28, 29 and 30 connected to a common display 31, as is indicated by the broken line 32. In the same manner, as indicated by the broken line 33, the different level indicators 28, 29 and 30 can also be connected to the microprocessor 4. As indicated by the broken lines 35, 36, 37, 38 and 39, the microprocessor 4 can be adapted to receive information from, or transmit information to, the valves 17, 18 and 19, the gas plate 1 and the ventilator section 3.

Turning now to FIG. 2, there is shown in more detail the construction of the gasification chamber 13. As shown, the gasification chamber 13 includes the heating plate 23 and the thermistor 24, or other such temperature measuring device. The heating plate 23 is heated by an element 40 which is connected via a cable 41 to the microprocessor 4. Collecting device 27, which is illustrated as a flask, is provided for the collection of any liquid which is not to be gasified. The gasification chamber 13 is further provided with a gas inlet 12a connected to the duct 12 and a gas outlet 42a connected to the duct 42. As shown in FIG. 1, the duct 42 is arranged communicating between the gasification chamber 13 and the ventilator section 3. Finally, a liquid inlet 43 is connected to one or more of ducts 20, 21 and 22. The heating plate 23 is arranged appropriately sloped in the direction towards the liquid collecting device 27. In addition, the heating plate 23 may be riffled or provided in some other manner with an enlarged surface to facilitate gasification.

The function of the anesthesia arrangement shown in accordance with the present invention should now be self-evident to those skilled in this art in the light of the foregoing description of the present invention. In this regard, the invention is particularly intended to be applied in connection with a complete anethesia arrangement of the type described in Swedish patent application Ser. No. 84.03449-5, filed on June 28, 1984, entitled "Anesthesia and/or Respirator Arrangement with Multi-Purpose Utilization the Treatment Gas" and U.S. patent application Ser. No. 748,772, filed on June 25, 1985, entitled "Anesthesia and/or Respirator arrangement with Alternative Manual Operation". The content of these patent applications is therefore incorporated in the present application by reference thereto.

It will be understood that the embodiments described herein are merely exemplary, and that a person skilled in the art may make many variations and modifications without departing from the spirit and scope of the invention. For example, the present invention may be used for other purposes than the gasification of anethetics, e.g., the clean moistening of respiratory gas in an ordinary respirator. All such modifications and variations are intended to be included within the scope of the invention, as defined in the appended claims.

What is claimed is:

1. Apparatus for supplying a gas stream to a patient comprising a source of a propellant gas; storage means for storing a gasifiable liquid; pressure means in fluid communication with said source for maintianing said liquid within said storage means under a pressure provided by said propellant gas, said liquid being supplied from said storage means in response to the pressure of said propellant gas acting on said liquid; a gasification chamber including a liquid inlet for receiving said liquid supplied from said storage means by said propellant gas, a gas inlet for receiving said propellant gas from said source and a gas stream outlet, said gasification chamber gasifying said liquid in the presence of said propellant gas supplied through said gas inlet to provide a gas stream therefrom to be supplied through said gas stream outlet to a patient; and metering means arranged between said liquid inlet and said storage means for metering the quantity of said liquid being supplied by said pressure means for said storage means to said gasification chamber.

2. The apparatus of claim 1 wherein said propellant gas maintaining said liquid under a pressure and said propellant gas provided to said gasification chamber are supplied from a common source.

3. The apparatus of claim 1 wherein said gasification chamber includes a heatable plate for heating said liquid to be gasified.

4. The apparatus of claim 3 further including temperature means for measuring the temperature of said heatable plate.

5. The apparatus of claim 1 wherein said storage means comprises a flask having an opening for receiving said pressure means therein.

6. The apparatus of claim 1 wherein said metering means is operable during a plurality of periods, whereby the supplying of said liquid from said storage means to said gasification chamber is a function of the duration of said periods.

7. The apparatus of claim 1 further including a plurality of said storage means for each storing a gasifiable liquid to be supplied to said gasification chamber.

8. The apparatus of claim 7 further including a plurality of liquid level indicators respectively associated with said plurality of said storage means for indicating the levels of said liquids therein, said levels being indicated on a common display.

9. The apparatus of claim 7 wherein said plurality of said storage means are connected alternatively to said liquid inlet of said gasification chamber.

10. The apparatus of claim 9 wherein said plurality of said storage means are separately connected to said liquid inlet through a corresponding number of said metering means.

11. The apparatus of claim 1 wherein said metering means comprises a valve.

12. The apparatus of claim 1 further including measuring means for measuring the energy used for gasifying said liquid by said gasification chamber for determining the quantity of said liquid being supplied thereto from said storage means.

13. The apparatus of claim 12 further including control means for generating an alarm signal when the amount of said energy measured differs from a predetermined limit value.

14. The apparatus of claim 13 further including adjustment means for adjusting said predetermined limit valve in relationship to the flow of said gas stream through said gasification chamber.

15. The apparatus of claim 14 wherein said predetermined limit value comprises a low limit value and a high limit value.

16. The apparatus of claim 13 wherein said gasification chamber includes a heatable plate for heating said liquid to be gasified.

17. The apparatus of claim 16 wherein said alarm is generated when $$\left| P_B \ddot{O}_R - P_{EL} \right| > K_4 + K_5 \times P_B \ddot{O}_R,$$

with $P_B \ddot{O}_R = P_O + K_1 \times F + K_2 \times M + K_3 (F,M)$ wherein:

$P_O$, $K_1$, $K_2$, $F_4$ and $K_5$ are constants,

F is the total gas flow through said gasification chamber,

M is the quantity of said liquid supplied per unit of time, $K_3$ is a connection value which is a function of F and M, $P_B \ddot{O}_R$ is the effect adapted to maintain said heatable plate at a constant temperature by the supply of said liquid to be gasified, and $P_{EL}$ is the corresponding measured value for said effect.

18. The apparatus of claim 1 further including temperature means for measuring the temperature of said gasification chamber.

19. The apparatus of claim 18 further including control means for generating an alarm signal when the value of the temperature measured differs from a predetermined limit value.

20. The apparatus of claim 19 wherein said gasification chamber includes a heatable plate for heating said liquid to be gasified and temperature measuring means for measuring the temperature of said heatable plate.

21. The apparatus of claim 20 wherein said alarm signal is generated when $$|U_T - K_6| > K_7 + K_8 \times P_{B\ddot{O}R},$$

wherein
- $K_6$, $K_7$ and $K_8$ are constants,
- $U_T$ is the measured voltage of said temperature measuring means, and
- $P_{B\ddot{O}R}$ is the effect adapted to maintain said heatable plate at a constant temperature by the supply of said liquid to be gasified.

22. The apparatus of claim 19 further including adjustment means for adjusting said predetermined limit value in relationship to the flow of said gas stream through said gasification chamber.

23. The apparatus of claim 22 wherein said predetermined limit value comprises a low limit value and a high limit value.

24. The apparatus of claim 1 further including collection means arranged in fluid communication with said gasification chamber for collecting non-gasified liquid within said chamber.

25. The apparatus of claim 1 further including a microprocessor adapted for controlling the operation of said gasification chamber.

* * * * *